(12) United States Patent
Cheung

(10) Patent No.: US 7,078,202 B2
(45) Date of Patent: *Jul. 18, 2006

(54) METHODS AND COMPOSITIONS FOR TREATING VASCULAR DEMENTIA

(75) Inventor: Ling Yuk Cheung, Hong Kong (HK)

(73) Assignee: Ultra Biotech Limited, Douglas (GB)

( * ) Notice: Subject to any disclaimer, the term of this patent is extended or adjusted under 35 U.S.C. 154(b) by 253 days.

This patent is subject to a terminal disclaimer.

(21) Appl. No.: 10/717,136

(22) Filed: Nov. 18, 2003

(65) Prior Publication Data

US 2005/0106170 A1 May 19, 2005

(51) Int. Cl.
*C12N 1/14* (2006.01)
*C12N 13/00* (2006.01)

(52) U.S. Cl. .................. 435/173.1; 435/255.1; 435/255.2; 435/173.8

(58) Field of Classification Search ............ 424/195.16; 435/173.1, 173.8, 255.1, 255.2
See application file for complete search history.

(56) References Cited

U.S. PATENT DOCUMENTS

| | | | |
|---|---|---|---|
| 2,107,830 A | 2/1938 | Liebesny et al. | |
| 3,150,979 A | 9/1964 | Ensley | |
| 3,711,392 A | 1/1973 | Metzger | |
| 3,870,599 A | 3/1975 | Azarowicz | |
| 3,923,279 A | 12/1975 | Gresley et al. | |
| 3,939,279 A | 2/1976 | Kawano et al. | |
| 3,968,254 A | 7/1976 | Rhodes et al. | |
| 3,997,675 A | 12/1976 | Eichelburg | |
| 4,041,182 A | 8/1977 | Erickson et al. | |
| 4,081,367 A | 3/1978 | Hulls et al. | 210/610 |
| 4,118,512 A | 10/1978 | Eichelburg | |
| 4,183,807 A | 1/1980 | Yoshizawa et al. | 210/611 |
| 4,211,645 A | 7/1980 | Zajic et al. | 210/611 |
| 4,348,483 A | 9/1982 | Skogerson | |
| 4,559,305 A | 12/1985 | Zajic et al. | 435/243 |
| 4,816,158 A | 3/1989 | Shimura et al. | 210/610 |
| 5,047,250 A | 9/1991 | Prieels et al. | |
| 5,075,008 A | 12/1991 | Chigusa et al. | 210/610 |
| 5,082,662 A | 1/1992 | Laurent et al. | |
| 5,082,936 A | 1/1992 | Jamas et al. | |
| 5,106,594 A | 4/1992 | Held et al. | 422/292 |
| 5,158,788 A | 10/1992 | Lavens et al. | |
| 5,416,010 A | 5/1995 | Langenberg et al. | 435/468 |
| 5,476,787 A | 12/1995 | Yokoyama et al. | 435/262.5 |
| 5,504,079 A | 4/1996 | Jamas et al. | |
| 5,567,314 A | 10/1996 | Chigusa et al. | 210/150 |
| 5,578,486 A | 11/1996 | Zhang | 435/243 |
| 5,665,352 A | 9/1997 | Blehaut et al. | |
| 5,707,524 A | 1/1998 | Potter | 210/606 |
| 5,866,116 A | 2/1999 | Yaegaki | |
| 5,879,928 A | 3/1999 | Dale et al. | 435/264 |
| 5,952,020 A | 9/1999 | Lizak | |
| 5,981,219 A | 11/1999 | Flugge et al. | |

(Continued)

FOREIGN PATENT DOCUMENTS

| | | |
|---|---|---|
| CN | 1110317 A | 10/1995 |
| CN | 1207873 | 2/1999 |
| CN | 1309175 | 8/2001 |
| EP | 0041373 | 12/1981 |
| EP | 553377 | 8/1993 |
| EP | 1375652 | 1/2004 |
| ES | 475500 | 4/1979 |
| FR | 2222433 | 10/1974 |
| GB | 1397873 | 6/1975 |
| JP | 60028893 | 2/1985 |
| SU | 415983 A | 11/1974 |
| SU | 1071637 | 2/1984 |
| SU | 1722364 | 3/1992 |
| SU | 1750570 | 7/1992 |
| WO | WO 87/02705 | 5/1987 |
| WO | WO 95/04814 | 2/1995 |
| WO | WO 99/60142 | 11/1999 |
| WO | WO 02/20431 | 3/2002 |
| WO | WO 02/62981 | 8/2002 |
| WO | WO 02/62982 | 8/2002 |
| WO | WO 02/62983 | 8/2002 |
| WO | WO 02/62984 | 8/2002 |
| WO | WO 02/62985 | 8/2002 |
| WO | WO02070436 | 9/2002 |
| WO | WO 02/070682 A2 | 9/2002 |
| WO | WO02070683 | 9/2002 |
| WO | WO2004108919 | 12/2004 |

OTHER PUBLICATIONS

Agarwal N. et al., "Selection of *Saccharomyces cerevisiae* strains for use as a microbial feed additive," *Letters in Applied Microbiology*, 31:270–273 (2000).

OTHER PUBLICATIONS

Asami, K. et al., "Real–Time Monitoring of Yeast Cell Division by Dielectric Spectroscopy", *Biophysical Journal*, 76, pp. 3345–3348 (1999).

Balcer–Kubiczek, E.K. et al., "Expression Analysis of Human HL60 Cells Exposed to 60 Hz Square–or Sine–Wave Magnetic Fields", *Radiation Research*, 153, pp. 670–678 (2000).

Bassett, C.A.L. et al., "Beneficial Effects of Electromagnetic Fields", *Journal of Cellular Biochemistry*, 51, pp. 387–393 (1993).

(Continued)

*Primary Examiner*—Christopher R. Tate
*Assistant Examiner*—Randall Winston
(74) *Attorney, Agent, or Firm*—Fish & Neave IP Group Ropes & Gray LLP; James F. Haley, Jr.; Z. Ying Li

(57) ABSTRACT

Compositions comprising a plurality of yeast cells, wherein said plurality of yeast cells have been cultured in the presence of an alternating electric field having a specific frequency and a specific field strength for a period of time sufficient to increase the capability of said plurality of yeast cells to treat vascular dementia in a mammal. Also included are methods of making such compositions and methods of treating vascular dementia.

13 Claims, 2 Drawing Sheets

U.S. PATENT DOCUMENTS

| | | | |
|---|---|---|---|
| 6,036,854 A | 3/2000 | Potter | 210/177 |
| 6,045,834 A | 4/2000 | Howes et al. | |
| 6,143,731 A | 11/2000 | Jamas et al. | |
| 6,159,510 A | 12/2000 | Lizak | |
| 6,197,295 B1 | 3/2001 | Hsia et al. | |
| 6,214,337 B1 | 4/2001 | Hayen et al. | |
| 6,391,617 B1 | 5/2002 | Cheung | 435/254 |
| 6,391,618 B1 | 5/2002 | Cheung | 435/255 |
| 6,391,619 B1 | 5/2002 | Cheung | 435/255 |
| 6,416,982 B1 | 7/2002 | Zhang | |
| 6,416,983 B1 | 7/2002 | Cheung | |
| 6,436,695 B1 | 8/2002 | Cheung | 435/254 |
| 6,440,713 B1 | 8/2002 | Cheung | 435/173 |
| 6,596,272 B1 | 7/2003 | Cheung | |
| 6,596,273 B1 | 7/2003 | Cheung | |
| 6,649,383 B1 | 11/2003 | Cheung | 435/173.1 |
| 6,660,508 B1 | 12/2003 | Cheung | 435/173.1 |
| 6,699,496 B1 | 3/2004 | Kojima et al. | |
| 6,761,886 B1 | 7/2004 | Cheung | |
| 6,800,466 B1 | 10/2004 | Cheung | |
| 6,828,131 B1 | 12/2004 | Zhang | |
| 6,828,132 B1 | 12/2004 | Cheung | |
| 2002/0099026 A1 | 7/2002 | Goodman et al. | |
| 2002/0123127 A1 | 9/2002 | Cheung | 435/254 |
| 2002/0123129 A1 | 9/2002 | Cheung | 435/254 |
| 2002/0123130 A1 | 9/2002 | Cheung | 435/262 |
| 2003/0230126 A1 | 12/2003 | Cheung | |
| 2003/0230245 A1 | 12/2003 | Cheung | |
| 2003/0232038 A1 | 12/2003 | Cheung | |
| 2003/0232039 A1 | 12/2003 | Cheung | |
| 2003/0232059 A1 | 12/2003 | Cheung | |
| 2003/0235565 A1 | 12/2003 | Cheung | |
| 2003/0235566 A1 | 12/2003 | Cheung | |
| 2003/0235567 A1 | 12/2003 | Cheung | |
| 2003/0235568 A1 | 12/2003 | Cheung | |
| 2003/0235569 A1 | 12/2003 | Cheung | |
| 2003/0235570 A1 | 12/2003 | Cheung | |
| 2004/0001812 A1 | 1/2004 | Cheung | |
| 2004/0001813 A1 | 1/2004 | Cheung | |
| 2004/0001814 A1 | 1/2004 | Cheung | |
| 2004/0001815 A1 | 1/2004 | Cheung | 424/93.51 |
| 2004/0001857 A1 | 1/2004 | Cheung | 424/195.16 |
| 2004/0001858 A1 | 1/2004 | Cheung | 424/195.16 |
| 2004/0001859 A1 | 1/2004 | Cheung | 424/195.16 |
| 2004/0001860 A1 | 1/2004 | Cheung | 424/195.16 |
| 2004/0001861 A1 | 1/2004 | Cheung | 424/195.16 |
| 2004/0005335 A1 | 1/2004 | Cheung | |
| 2004/0005337 A1 | 1/2004 | Cheung | 424/195.16 |
| 2004/0005680 A1 | 1/2004 | Cheung | |
| 2004/0168492 A1 | 9/2004 | Cheung | |
| 2004/0252492 A1 | 12/2004 | Cheung | |
| 2004/0253251 A1 | 12/2004 | Cheung | |
| 2004/0253252 A1 | 12/2004 | Cheung | |
| 2004/0253253 A1 | 12/2004 | Cheung | |
| 2004/0253254 A1 | 12/2004 | Cheung | |
| 2004/0253255 A1 | 12/2004 | Cheung | |
| 2004/0253256 A1 | 12/2004 | Cheung | |
| 2004/0253257 A1 | 12/2004 | Cheung | |
| 2004/0253258 A1 | 12/2004 | Cheung | |
| 2004/0253259 A1 | 12/2004 | Cheung | |
| 2004/0253260 A1 | 12/2004 | Cheung | |
| 2004/0253261 A1 | 12/2004 | Cheung | |
| 2004/0253262 A1 | 12/2004 | Cheung | |
| 2004/0253263 A1 | 12/2004 | Cheung | |
| 2004/0253264 A1 | 12/2004 | Cheung | |
| 2004/0253265 A1 | 12/2004 | Cheung | |
| 2004/0253266 A1 | 12/2004 | Cheung | |
| 2004/0253267 A1 | 12/2004 | Cheung | |
| 2004/0253268 A1 | 12/2004 | Cheung | |
| 2004/0265990 A1 | 12/2004 | Cheung | |

Binninger, D. M. et al., "Effects of 60Hz AC magnetic fields on gene expression following exposure over multiple cell generations using *Saccharomyces cerevisiae*", *Bioelectrochemistry and Bioenergetics*, 43(1): 83–89 (1997).

Conti, P. et al., "Effect of Electromagnetic Fields on Several CD Markers and Transcription and Expression of CD4", *Immunobiology*, 201, pp. 36–48 (1999).

Deguchi, T. et al., "Nylon biodegradation by lignin–degrading fungi", *Applied and Environmental Microbiology*, 63(1): 329–331 (1997).

Dufresne C. et al., "Tea, Kombucha, and Health: A review," *Food Research International*, 33:409–421 (2000).

Gonzalez, A.M. et al., "Effects of an Electric Field of Sinusoidal Waves on the Amino Acid Biosynthesis by Azotobacter", *Z. Naturforsch*, 35, pp. 258–261 (1980).

Goodman, E.M. et al., "Effects of Electromagnetic Fields on Molecules and Cells", *International Review of Cytology*, 158, pp. 279–339 (1995).

Greenwalt C.J. et al., "Kombucha, the fermented tea: Microbiology, composition, and claimed health effects," *Journal of Food Protection*, 63:976–981 (2000).

Grospietsch, T. et al., "Stimulating Effects of Modulated 150 MHz Electromagnetic Fields on the Growth of *Escherichia coli* in a Cavity Resonator", *Bioelectrochemistry and Bioenergetics*, 37, pp. 17–23 (1995).

Grundler W. et al., "Resonant–like dependence at yeast growth rate on microwave frequencies," *The British Journal of Cancer*, Supplement, England Mar. 1982, 45:206–208 (1982).

Grundler, W. et al., "Mechanisms of Electromagnetic Interaction with Cellular Systems", *Naturwissenschaften*, 79, pp. 551–559 (1992).

Grundler, W. et al., "Nonthermal Effects of Millimeter Microwaves on Yeast Growth", *Z. Naturforsch*, 33, pp. 15–22 (1978).

Ivaschuk, O.I. et al., "Exposure of Nerve Growth Factor–Treated PC12 Rat Pheochromocytoma Cells to a Modulated Radiofrequency Field at 836.55 MHz: Effects on c–jun and c–fos Expression", *Bioelectromagnetics*, 18, pp. 223–229 (1997).

Jelinek, F. et al., "Microelectronic Sensors for Measurement of Electromagnetic Fields of Living Cells and Experimental Results", *Bioelectrochemistry and Bioenergetics*, 48, pp. 261–266 (1999).

Lacy–Hulbert, A. et al., "Biological Responses to Electromagnetic Fields", *FASEB Journal*, 12, pp. 395–420 (1998).

Libertin, C.R. et al., "Effects of Gamma Rays, Ultraviolet Radiation, Sunlight, Microwaves and Electromagnetic Fields on Gene Expression Mediated by Human Immunodeficiency Virus Promoter", *Radiation Research*, 140, pp. 91–96 (1994).

Lin, H. et al., "Magnetic Field Activation of Protein–DNA Binding", *Journal of Cellular Biochemistry*, 70, pp. 297–303 (1998).

Lin, H. et al., "Specific Region of the c–myc Promoter is Responsive to Electric and Magnetic Fields", *Journal of Cellular Biochemistry*, 54, pp. 281–288 (1994).

Liu C.H. et al., "The Isolation and identification of microbes from a fermented tea beverage, Haipao, and their interactions during Haipao fermentation," *Food Microbiology* (London), 13:407–415 (1996).

Loberg, L.I. et al., "Expression of Cancer–Related Genes in Human Cells Exposed to 60 Hz Magnetic Fields", *Radiation Research*, 153, pp. 679–684 (2000).

Mayser P. et al., "The yeast spectrum of the 'tea fungus Kombucha'," *Mycoses*, Blackwell, Berlin, Germany, 38:289–295 (1995).

Moore, R.L., "Biological Effects of Magnetic Fields: Studies with Microorganisms", *Canadian Journal of Microbiology*, 25, pp. 1145–1151 (1979).

Morehouse, C.A. et al., "Exposure of Daudi Cells to Low-Frequency Magnetic Fields Does Not Elevate MYC Steady-State mRNA Levels", *Radiation Research*, 153, pp. 663–669 (2000).

Norris, V. et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879–880 (1997).

Novelli, G. et al., "Study of the Effects of DNA of Electromagnetic Fields Using Clamped Homogeneous Electric Field Gel Electrophoresis", *Biomedicine & Pharmacotherapy*, 45, pp. 451–454 (1991).

Phillips, J.L., "Effects of Electromagnetic Field Exposure on Gene Transcription", *Journal of Cellular Biochemistry*, 51, pp. 381–386 (1993).

Pichko, V. B. et al., "Electromagnetic stimulation of productivity of microorganisms and its mechanisms", *Prikladnaya Biokhimiya I Mikrobiologiya*, 32(4): 468–472 (1996).

Ponne, C. T. et al., "Interaction of electromagnetic energy with biological material-relation to food processing", *Radiation Physica and Chemistry*, 45(4): 591–607 (1995).

Romano–Spica, V. et al., "Ets1 Oncogene Induction by ELF-Modulated 50 MHz Radiofrequency Electromagnetic Field", *Bioelectromagnetics*, 21, pp. 8–18 (2000).

Surawicz Christina M. et al., "The search for a better treatment for recurrent Clostridium difficile disease: Use of high-dose vancomycin combined with *Saccharomyces boulardii*," *Clinical Infectious Diseases*, 31:1012–1017 (2000).

Trosko, J.E., "Human Health Consequences of Environmentally-Modulated Gene Expression: Potential Roles of ELF-EMF Induced Epigenetic Versus Mutagenic Mechanisms of Disease", *Bioelectromagnetics*, 21, pp. 402–406 (2000).

Van den Bogaerde J. et al., "Immune sensitization to food, yeast and bacteria in Crohn's disease," *Alimentary Pharmacology & Therapeutics*, 15:1647–1653 (2001).

Van Rensburg, P. et al., "Engineering yeast for efficient cellulose degradation", *Yeast*, 14(1): 67–76 (1998).

Ventura, C. et al., "Elf-pulsed Magnetic Fields Modulate Opioid Peptide Gene Expression in Myocardial Cells", *Cardiovascular Research*, 45, pp. 1054–1064 (2000).

Woodward, A.M. et al., "Genetic Programming as an Analytical Tool for Non-linear Dielectric Spectroscopy", *Bioelectrochemistry and Bioenergetics*, 48, pp. 389–396 (1999).

Yonetani, T. et al., "Electromagnetic Properties of Hemoproteins", *The Journal of Biological Chemistry*, 247, pp. 2447–2455 (1972).

Zhang, L. et al., "Electrostimulation of the Dehydrogenase System of Yeast by Alternating Currents", *Bioelectrochemistry and Bioenergetics*, 28, pp. 341–353 (1992).

"*Saccharomyces cerevisiae* Meyen ex Hansen", China Catalogue of Cultures/China Committee of Culture Collection of Microorganisms (CCCCM), "www.im.ac.cn/database/YEAST/y122.htm", Apr. 24, 1996, retrieved on Nov. 27, 2002.

U.S. Appl. No. 10/192,805 filed Nov. 29, 2004, Zhang.

U.S. Appl. No. 10/192,807 filed Nov. 29, 2004, Cheung.

Born et al., "The *Saccharomyces boulardii* Therapy of HIV-Associated Diarrhea", *Deutsche Medizinische Wochenschrift*, 118(20):765 (1993). (in German with English translation).

Dutta et al., *J. of Microwave Power*, vol. 14, No. 3, pp. 275–280 (1979).

Goodman, et al., "Magnetic Field Stress Induces Expression of HSP70", *Cell Stress & Chaperones* 3(2):79–88 (1998).

Grundler W., "Resonant Microwave Effect on Locally Fixed Yeast Microcolonies" *Z. Naturforsch* 44c:863–866 (1989).

Kim et al., "Anti-Stress and Anti-Fatigue Effects of Fermented Rice Bran", *Biosci Biotechnol Biochem.*, 65(10):2294–6 (2001).

Lin H. et al., "A Magnetic Field-Responsive Domain in the Human HSP70 Promoter", *J Cell Biochem*, 75:170–176 (1999).

Machado Caetano et al., "Immunopharmacological Effects of *Sacchoramyces boulardii* in Healthy Human Volunteers", *Int'l Immunology and Immunopharmacology*, 8(3):245–259 (1986).

Ortuno et al., "Oral Administration of Yeast, *Saccharomyces cerevisiae*, Enhances the Cellular Innate Immune response of Gilthead Seabream (*Sparus aurate* L.)", *Vet Immunol Immunopathol*, 85(1–2):41–50 (2002).

Peret Filho et al., "Dose Effect of Oral *Saccharomyces boulardii* Treatments on Morbidity and Mortality in Immunosuppressed Mice", *J Med Microbiol.*, 47(2):111–6 (1998).

Saha et al., "Microbial Manipulation of Rumen Fermentation Using *Saccharomyces cerevisiae* as Probiotics", *Current Science* (Bangalore), 77(5):696–697 (1999).

WHO World Health Organization; WebPages http:www.who.int/peh–emf/about/WhatisEMF/en/ and http:www.who.int/peh–emf/about/WhatisEMF/en/index3.html retrieved Jun. 10, 2004.

METHODS AND COMPOSITIONS FOR TREATING VASCULAR DEMENTIA

FIELD OF THE INVENTION

The invention relates to compositions that treat vascular dementia and can be taken as dietary supplements or medication. The compositions comprise yeast cells obtainable by growth in electromagnetic fields with specific frequencies and field strengths.

BACKGROUND OF THE INVENTION

Vascular Dementia (VaD) is defined as the loss of cognitive function resulting from ischemic, ischemic-hypoxic, or hemorrhagic brain lesions as a result of cardiovascular diseases and cardiovascular pathologic changes. See, e.g., G. C. Roman, *Med. Clin. North. Am.,* 86, pp. 477–99 (2002). VaD is a chronic disorder and the symptoms of VaD include cognitive loss, headaches, insomnia and memory loss. VaD may be caused by multiple strokes (MID or poststroke dementia) but also by single strategic strokes, multiple lacunes, and hypoperfusive lesions such as border zone infarcts and ischemic periventricular leukoencephalopathy (Binswanger's disease). See, G. C. Roman, supra. In Asian countries such as China, Japan and Korea, VaD is observed in over 60% of patients with dementia. Primary and secondary prevention of stroke and cardiovascular disease decreases the burden of VaD.

Treatment of VaD involves control of risk factors (i.e., hypertension, diabetes, smoking, hyperfibrinogenemia, hyperhomocystinemia, orthostatic hypotension, cardiac arrhythmias). See, G. C. Roman, supra. Researchers have also investigated whether hormone replacement therapy and estrogen replacement therapy could delay the onset of dementia in women. See, E. Hogervorst et al., *Cochrane Database Syst. Rev.,* 3, CD003799 (2002). Although there has been evidence that aspirin is widely prescribed for VaD, there is very limited evidence that aspirin is effective in treating patients with VaD. See, P. S. Williams et al., *Cochrane Database Syst. Rev.,* 2, CD001296 (2000). Nimodipine has been implicated as a drug demonstrating short-term benefits in VaD patients, but has not been justified as a long-term anti-dementia drug. See, J. M. Lopez-Arrieta and J. Birks, *Cochrane Database Syst. Rev.,* 3, CD000147 (2002). Further, clinical efficacy data of piracetam does not support the use of this drug in the treatment of dementia or cognitive impairment. L. Flicker and G. Grimley Evans, *Cochrane Database Syst. Rev.,* 2, CD001011 (2001). Thus, an agent that is effective in treating VaD is highly desired in the market.

SUMMMARY OF THE INVENTION

This invention is based on the discovery that certain yeast cells can be activated by electromagnetic fields having specific frequencies and field strengths to produce substances that assist in treating vascular dementia. The composition of this invention can be taken as dietary supplements in the form of health drinks or pills.

This invention embraces a composition comprising a plurality of yeast cells that have been cultured in the presence of an alternating electric field having a frequency in the range of about 10280 to 13000 MHz and a field strength in the range of about 200 to 500 mV/cm, as compared to yeast cells not having been so cultured. In one embodiment, the frequency of the culturing is in the range of about 10280 to 10400 MHz, 12320 to 12380 MHz or 12950 to 13000 MHz. In one embodiment, the field strength is in the range of about 200 to 400 mV/cm. The yeast cells are cultured in the alternating electric field for a period of time sufficient to increase the capability of said plurality of yeast cells to improve the memory of a mammal with vascular dementia, as compared to unactivated yeast cells. Preferably, the mammal is human. In one embodiment, the vascular dementia was induced by cerebral ischemia. In another embodiment, the vascular dementia was induced by blockage of the middle cerebral artery. In one embodiment, the frequency and/or the field strength of the alternating electric field can be altered within the aforementioned ranges during said period of time. In other words, the yeast cells can be exposed to a series of electromagnetic fields. An exemplary period of time is about 80–140 hours.

Also included in this invention is a composition comprising a plurality of yeast cells that have been cultured under acidic conditions in an alternating electric field having a frequency in the range of about 12950–13000 MHz and a field strength in the range of about 240 to 460 mV/cm (e.g., 240–260, 320–350, 360–390 or 420–460 mV/cm). In one embodiment, the yeast cells are exposed to a series of electromagnetic fields. An exemplary period of time is about 80–190 hours.

Included in this invention are also methods of making the above compositions and methods of treating vascular dementia.

Yeast cells that can be included in this composition can all be derived from the China General Microbiological Culture Collection Center ("CGMCC") (China Committee for Culture Collection of Microorganisms, Institute of Microbiology, Chinese Academy of Sciences, Haidian, P.O. BOX 2714, Beijing, 100080, China). Useful yeast species include, but are not limited to, *Schizosaccharomyces pombe, Saccharomyces sake, Saccharomyces uvarum, Saccharomyces rouxii, Saccharomyces carlsbergensis, Rhodotorula aurantiaca* and *Saccharomyces cerevisiae*. For instance, the yeast cells can be of the strain *Saccharomyces cerevisiae* Hansen IFF11340. In another embodiment, the yeast cells are from the strains selected from the group consisting of *Saccharomyces cerevisiae* Hansen AS 2.501, AS2.502, AS2.503, AS2.504, AS2.535, AS2.558, AS2.560, AS2.561 and AS2.562. Other useful yeast species are illustrated in Table 1.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

Other features and advantages of the invention will be apparent from the following detailed description, and from the claims.

DETAILED DESCRIPTION OF THE INVENTION

Figure 1:
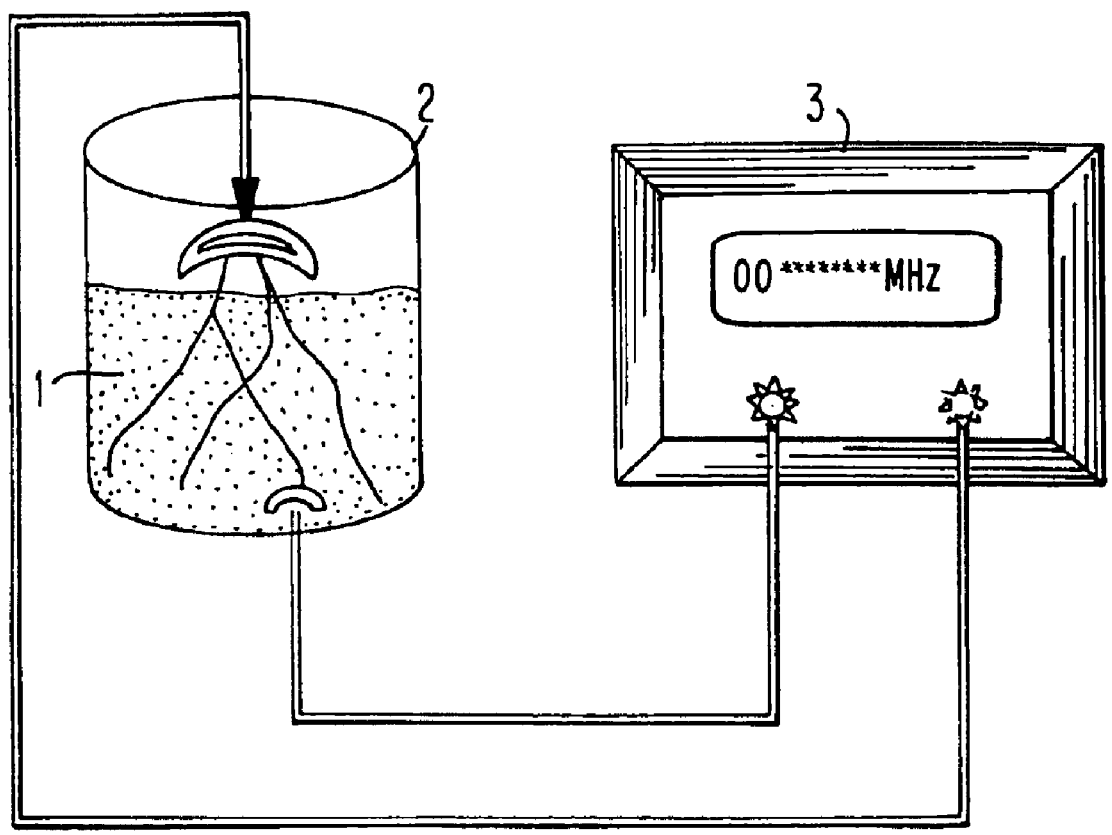
FIG. 1 is a schematic diagram showing an exemplary apparatus for activating yeast cells using electromagnetic fields. 1: yeast culture; 2: container; 3: power supply.

This invention is based on the discovery that certain yeast strains can be activated by electromagnetic fields ("EMF") having specific frequencies and field strengths to produce agents useful in improving the memory of a mammal with vascular dementia. Yeast compositions containing activated yeast cells can be used as medication, or as dietary supplements in the form of, e.g., health drinks or dietary pills.

Since the activated yeast cells contained in these yeast compositions have been cultured to endure acidic conditions of pH 2.5–4.2, the compositions are stable in the stomach and can pass on to the intestines. Once in the intestines, the yeast cells are ruptured by various digestive enzymes, and the agents useful in improving memory are released and readily absorbed.

I. Yeast Strains Useful in the Invention

The types of yeasts useful in this invention include, but are not limited to, yeasts of the genera *Saccharomyces*, *Schizosaccharomyces* and *Rhodotorula*.

Exemplary species within the above-listed genera include, but are not limited to, the species illustrated in Table 1. Yeast strains useful in this invention can be obtained from laboratory cultures, or from publically accessible culture depositories, such as CGMCC and the American Type Culture Collection, 10801 University Boulevard, Manassas, Va. 20110-2209. Non-limiting examples of useful strains (with the accession numbers of CGMCC) are illustrated in Table 1. In general, yeast strains preferred in this invention are those used for fermentation in the food and wine industries. As a result, compositions containing these yeast cells are safe for human consumption. The preparation of the yeast compositions of this invention is not limited to starting with a pure strain of yeast. A yeast composition of the invention may be produced by culturing a mixture of yeast cells of different species or strains.

TABLE 1

Exemplary Yeast Strains

*Saccharomyces cerevisiae* Hansen

| | | | | |
|---|---|---|---|---|
| ACCC2034 | ACCC2035 | ACCC2036 | ACCC2037 | ACCC2038 |
| ACCC2039 | ACCC2040 | ACCC2041 | ACCC2042 | AS2.1 |
| AS2.4 | AS2.11 | AS2.14 | AS2.16 | AS2.56 |
| AS2.69 | AS2.70 | AS2.93 | AS2.98 | AS2.101 |
| AS2.109 | AS2.110 | AS2.112 | AS2.139 | AS2.173 |
| AS2.174 | AS2.182 | AS2.196 | AS2.242 | AS2.336 |
| AS2.346 | AS2.369 | AS2.374 | AS2.375 | AS2.379 |
| AS2.380 | AS2.382 | AS2.390 | AS2.393 | AS2.395 |
| AS2.396 | AS2.397 | AS2.398 | AS2.399 | AS2.400 |
| AS2.406 | AS2.408 | AS2.409 | AS2.413 | AS2.414 |
| AS2.415 | AS2.416 | AS2.422 | AS2.423 | AS2.430 |
| AS2.431 | AS2.432 | AS2.451 | AS2.452 | AS2.453 |
| AS2.458 | AS2.460 | AS2.463 | AS2.467 | AS2.486 |
| AS2.501 | AS2.502 | AS2.503 | AS2.504 | AS2.516 |
| AS2.535 | AS2.536 | AS2.558 | AS2.560 | AS2.561 |
| AS2.562 | AS2.576 | AS2.593 | AS2.594 | AS2.614 |
| AS2.620 | AS2.628 | AS2.631 | AS2.666 | AS2.982 |
| AS2.1190 | AS2.1364 | AS2.1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |
| IFFI1043 | IFFI1045 | IFFI1048 | IFFI1049 | IFFI1050 |
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI1211 | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | IFFI1337 | IFFI1338 | IFFI1339 | IFFI1340 |
| IFFI1345 | IFFI1348 | IFFI1396 | IFFI1397 | IFFI1399 |
| IFFI1411 | IFFI1413 | IFFI1441 | IFFI1443 | |
| *Saccharomyces cerevisiae* Hansen Var. *ellipsoideus* (Hansen) Dekker | | | | |
| ACCC2043 | AS2.2 | AS2.3 | AS2.8 | AS2.53 |
| AS2.163 | AS2.168 | AS2.483 | AS2.541 | AS2.559 |
| AS2.606 | AS2.607 | AS2.611 | AS2.612 | |
| *Saccharomyces chevalieri* Guilliermond | | | | |
| AS2.131 | AS2.213 | | | |
| *Saccharomyces delbrueckii* | | | | |
| AS2.285 | | | | |

TABLE 1-continued

Exemplary Yeast Strains

*Saccharomyces delbrueckii* Lindner ver. *mongolicus* (Saito) Lodder et van Rij

| | | | | |
|---|---|---|---|---|
| AS2.209 | AS2.1157 | | | |

*Saccharomyces exiguous* Hansen

| | | | | |
|---|---|---|---|---|
| AS2.349 | AS2.1158 | | | |

*Saccharomyces fermentati* (Saito) Lodder et van Rij

| | | | | |
|---|---|---|---|---|
| AS2.286 | AS2.343 | | | |

*Saccharomyces logos* van laer et Denamur ex Jorgensen

| | | | | |
|---|---|---|---|---|
| AS2.156 | AS2.327 | AS2.335 | | |

*Saccharomyces mellis* (Fabian et Quinet) Lodder et kreger van Rij

| | | | | |
|---|---|---|---|---|
| AS2.195 | | | | |

*Saccharomyces mellis Microellipsoides* Osterwalder

| | | | | |
|---|---|---|---|---|
| AS2.699 | | | | |

*Saccharomyces oviformis* Osteralder

| | | | | |
|---|---|---|---|---|
| AS2.100 | | | | |

*Saccharomyces rosei* (Guilliermond) Lodder et Kreger van Rij

| | | | | |
|---|---|---|---|---|
| AS2.287 | | | | |

*Saccharomyces rouxii* Boutroux

| | | | | |
|---|---|---|---|---|
| AS2.178 | AS2.180 | AS2.370 | AS2.371 | |

*Saccharomyces sake* Yabe

| | | | | |
|---|---|---|---|---|
| ACCC2045 | | | | |

*Candida arborea*

| | | | | |
|---|---|---|---|---|
| AS2.566 | | | | |

*Candida lambica* (Lindner et Genoud) van. Uden et Buckley

| | | | | |
|---|---|---|---|---|
| AS2.1182 | | | | |

*Candida krusei* (Castellani) Berkhout

| | | | | |
|---|---|---|---|---|
| AS2.1045 | | | | |

*Candida lipolytica* (Harrison) Diddens et Lodder

| | | | | |
|---|---|---|---|---|
| AS2.1207 | AS2.1216 | AS2.1220 | AS2.1379 | AS2.1398 |
| AS2.1399 | AS2.1400 | | | |

*Candida parapsilosis* (Ashford) Langeron et Talice Var. *intermedia* Van Rij et Verona

| | | | | |
|---|---|---|---|---|
| AS2.491 | | | | |

*Candida parapsilosis* (Ashford) Langeron et Talice

| | | | | |
|---|---|---|---|---|
| AS2.590 | | | | |

*Candida pulcherrima* (Lindner) Windisch

| | | | | |
|---|---|---|---|---|
| AS2.492 | | | | |

*Candida rugousa* (Anderson) Diddens et Lodder

| | | | | |
|---|---|---|---|---|
| AS2.511 | AS2.1367 | AS2.1369 | AS2.1372 | AS2.1373 |
| AS2.1377 | AS2.1378 | AS2.1384 | | |

*Candida tropicalis* (Castellani) Berkhout

| | | | | |
|---|---|---|---|---|
| ACCC2004 | ACCC2005 | ACCC2006 | AS2.164 | AS2.402 |
| AS2.564 | AS2.565 | AS2.567 | AS2.568 | AS2.617 |
| AS2.637 | AS2.1387 | AS2.1397 | | |

*Candida utilis* Henneberg Lodder et Kreger Van Rij

| | | | | |
|---|---|---|---|---|
| AS2.120 | AS2.281 | AS2.1180 | | |

*Crebrothecium ashbyii* (Guilliermond)
Routein (*Eremothecium ashbyii* Guilliermond)

| | | | | |
|---|---|---|---|---|
| AS2.481 | AS2.482 | AS2.1197 | | |

*Geotrichum candidum* Link

| | | | | |
|---|---|---|---|---|
| ACCC2016 | AS2.361 | AS2.498 | AS2.616 | AS2.1035 |
| AS2.1062 | AS2.1080 | AS2.1132 | AS2.1175 | AS2.1183 |

*Hansenula anomala* (Hansen)H et P sydow

| | | | | |
|---|---|---|---|---|
| ACCC2018 | AS2.294 | AS2.295 | AS2.296 | AS2.297 |
| AS2.298 | AS2.299 | AS2.300 | AS2.302 | AS2.338 |

TABLE 1-continued

Exemplary Yeast Strains

| AS2.339 | AS2.340 | AS2.341 | AS2.470 | AS2.592 |
| AS2.641 | AS2.642 | AS2.782 | AS2.635 | AS2.794 |

*Hansenula arabitolgens* Fang

AS2.887

*Hansenula jadinii* (A. et R Sartory Weill et Meyer) Wickerham

ACCC2019

*Hansenula saturnus* (Klocker) H et P sydow

ACCC2020

*Hansenula schneggii* (Weber) Dekker

AS2.304

*Hansenula subpelliculosa* Bedford

| AS2.740 | AS2.760 | AS2.761 | AS2.770 | AS2.783 |
| AS2.790 | AS2.798 | AS2.866 | | |

*Kloeckera apiculata* (Reess emend. Klocker) Janke

| ACCC2022 | ACCC2023 | AS2.197 | AS2.496 | AS2.714 |
| ACCC2021 | AS2.711 | | | |

*Lipomycess starkeyi* Lodder et van Rij

AS2.1390    ACCC2024

*Pichia farinosa* (Lindner) Hansen

| ACCC2025 | ACCC2026 | AS2.86 | AS2.87 | AS2.705 |
| AS2.803 | | | | |

*Pichia membranaefaciens* Hansen

| ACCC2027 | AS2.89 | AS2.661 | AS2.1039 | |

*Rhodosporidium toruloides* Banno

ACCC2028

*Rhodotorula glutinis* (Fresenius) Harrison

| AS2.2029 | AS2.280 | ACCC2030 | AS2.102 | AS2.107 |
| AS2.278 | AS2.499 | AS2.694 | AS2.703 | AS2.704 |
| AS2.1146 | | | | |

*Rhodotorula minuta* (Saito) Harrison

AS2.277

*Rhodotorula rubar* (Demme) Lodder

| AS2.21 | AS2.22 | AS2.103 | AS2.105 | AS2.108 |
| AS2.140 | AS2.166 | AS2.167 | AS2.272 | AS2.279 |
| AS2.282 | ACCC2031 | | | |

*Rhodotorula aurantiaca* (Saito) Lodder

| AS2.102 | AS2.107 | AS2.278 | AS2.499 | AS2.694 |
| AS2.703 | AS2.1146 | | | |

*Saccharomyces carlsbergensis* Hansen

| AS2.113 | ACCC2032 | ACCC2033 | AS2.312 | AS2.116 |
| AS2.118 | AS2.121 | AS2.132 | AS2.162 | AS2.189 |
| AS2.200 | AS2.216 | AS2.265 | AS2.377 | AS2.417 |
| AS2.420 | AS2.440 | AS2.441 | AS2.443 | AS2.444 |
| AS2.459 | AS2.595 | AS2.605 | AS2.638 | AS2.742 |
| AS2.745 | AS2.748 | AS2.1042 | | |

*Saccharomyces uvarum* Beijer

| IFFI1023 | IFFI1032 | IFFI1036 | IFFI1044 | IFFI1072 |
| IFFI1205 | IFFI1207 | | | |

*Saccharomyces willianus* Saccardo

| AS2.5 | AS2.7 | AS2.119 | AS2.152 | AS2.293 |
| AS2.381 | AS2.392 | AS2.434 | AS2.614 | AS2.1189 |

*Saccharomyces* sp.

AS2.311

*Saccharomycodes ludwigii* Hansen

ACCC2044    AS2.243    AS2.508

TABLE 1-continued

Exemplary Yeast Strains

*Saccharomycodes sinenses* Yue

AS2.1395

*Schizosaccharomyces octosporus* Beijerinck

ACCC2046    AS2.1148

*Schizosaccharomyces pombe* Lindner

| ACCC2047 | ACCC2048 | AS2.214  | AS2.248  | AS2.249 |
|----------|----------|----------|----------|---------|
| AS2.255  | AS2.257  | AS2.259  | AS2.260  | AS2.274 |
| AS2.994  | AS2.1043 | AS2.1149 | AS2.1178 | IFFI1056 |

*Sporobolomyces roseus* Kluyver et van Niel

| ACCC2049 | ACCC2050 | AS2.19   | AS2.962  | AS2.1036 |
|----------|----------|----------|----------|----------|
| ACCC2051 | AS2.261  | AS2.262  |          |          |

*Torulopsis candida* (Saito) Lodder

AS2.270     ACCC2052

*Torulopsis famta* (Harrison) Lodder et van Rij

ACCC2053    AS2.685

*Torulopsis globosa* (Olson et Hammer) Lodder et van Rij

ACCC2054    AS2.202

*Torulopsis inconspicua* Lodder et Kreger van Rij

AS2.75

*Trichosporon behrendii* Lodder et Kreger van Rij

ACCC2056    AS2.1193

*Trichosporon capitatum* Diddens et Lodder

ACCC2056    AS2.1385

*Trichosporon cutaneum* (de Beurm et al.) Ota

| ACCC2057 | AS2.25 | AS2.570 | AS2.571 | AS2.1374 |

*Wickerhamia fluorescens* (Soneda) Soneda

ACCC2058    AS2.1388

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag—AgCl electrodes in solutions rich in chloride ions, and run at as low a voltage as possible. For general review, see Goodman et al., *Effects of EMF on Molecules and Cells*, International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 10280 to 13000 MHz (e.g., 10280 to 10400, 12320 to 12380 and 12950 to 13000 MHz). Exemplary frequencies include 10300, 10312, 12348, 12963 and 12987 MHz. The field strength of the electric field useful in this invention ranges from about 200 to 500 mV/cm (e.g., 240–260, 270–290 and 330–480 mV/cm). Exemplary field strengths include 256, 282, 332, 337, 343, 356, 367, 372, 382, 416, 435 and 461 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above-described ranges. Although any practical number of EMFs can be used in a series, it may be preferred that the yeast culture be exposed to a total of 2, 3, 4, 5, 6, 7, 8, 9, 10, 11, 12, 13 or more EMFs in a series. In one embodiment, the yeast culture is exposed to a series of EMFs, wherein the frequency of the electric field is alternated in the range of about 10280 to 10400, 12320 to 12380 and 12950 to 13000 MHz.

Although the yeast cells can be activated after even a few hours of culturing in the presence of an EMF, it may be preferred that the compositions comprising activated yeast cells be allowed to multiply and grow in the presence of the EMF(s) for a total of 80–140, 90–136 and 80–190 hours.

FIG. 1 illustrates an exemplary apparatus for generating alternating electric fields. An electric field of a desired frequency and intensity can be generated by an AC source (3) capable of generating an alternating electric field, preferably in a sinusoidal wave form, in the frequency range of 5 to 20,000 MHz. Signal generators capable of generating signals with a narrower frequency range can also be used. If desired, a signal amplifier can also be used to increase the output. The culture container (2) can be made from a non-conductive material, e.g., glass, plastic or ceramic. The cable connecting the culture container (2) and the signal generator (3) is preferably a high frequency coaxial cable with a transmission frequency of at least 20 GHz. In one embodiment, the transmission frequency is 30 GHz.

The alternating electric field can be applied to the culture by a variety of means, including placing the yeast culture (1) in close proximity to the signal emitters such as a metal wire or tube capable of transmitting EMFs. The metal wire or tube can be made of red copper, and be placed inside the container (2), reaching as deep as 3–30 cm. For example, if the fluid in the container (2) has a depth of 15–20 cm, 20–30 cm, 30–50 cm, 50–70 cm, 70–100 cm, 100–150 cm or 150–200 cm, the metal wire can be 3–5 cm, 5–7 cm, 7–10 cm, 10–15 cm, 15–20 cm, 20–30 cm and 25–30 cm from the bottom of the container (2), respectively. The number of metal wires/tubes used can be from 1 to 10 (e.g., 2 to 3). It is recommended, though not mandated, that for a culture having a volume up to 10 L, metal wires/tubes having a diameter of 0.5 to 2 mm be used. For a culture having a volume of 10–100 L, metal wires/tubes having a diameter of 3 to 5 mm can be used. For a culture having a volume of 100–1000 L, metal wires/tubes having a diameter of 6 to 15 mm can be used. For a culture having a volume greater than 1000 L, metal wires/tubes having a diameter of 20–25 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy. The number of electrode wires used depends on the volume of the culture as well as the diameter of the wires.

III. Culture Media

Culture media useful in this invention contain sources of nutrients that can be assimilated by yeast cells. Complex carbon-containing substances in a suitable form (e.g., carbohydrates such as sucrose, glucose, dextrose, maltose, starch, xylose; mannitol) can be the carbon sources for yeast cells. The exact quantity of the carbon sources can be adjusted in accordance with the other ingredients of the medium. In general, the amount of carbon-containing substances varies between about 0.5% and 10% by weight of the medium, and preferably between about 1% and 5%, and most preferably between about 1.0–2.5%. These carbon sources can be used individually or in combination. Vitamins can also be added to the medium, for example, Vitamin D, Vitamin $B_{22}$, Vitamin E or Vitamin $B_6$. Among the inorganic salts which can be added to a culture medium are the customary salts capable of yielding sodium, potassium, calcium, phosphate, sulfate, carbonate, and like ions. Non-limiting examples of nutrient inorganic salts are $(NH_4)_2HPO_4$, $CaCO_3$, $KH_2PO_4$, $K_2HPO_4$, $MgSO_4$, NaCl, and $CaSO_4$.

IV. Electromagnetic Activation of Yeast Cells

To activate or enhance the innate ability of yeast cells to improve memory, these cells can be cultured in an appropriate medium under sterile conditions at 20° C.–35° C. (e.g., 28–32° C.) for a sufficient amount of time, e.g., 80–140, 90–136, 80–190 hours, in an alternating electric field or a series of alternating electric fields as described above.

An exemplary set-up of the culture process is depicted in FIG. 1 (see above). An exemplary culture medium contains the following in per 1000 ml of sterile water: 6 g of sucrose, 12 g of mannitol, 70 μg of Vitamin D, 50 μg of Vitamin $B_{12}$, 40 μg of Vitamin E, 90 μg of Vitamin $B_6$, 50 ml of bovine serum, 0.20 g of $KH_2PO_4$, 0.25 g of $MgSO_4.7H_2O$, 0.3 g of NaCl, 0.2 g of $CaSO_4.2H_2O$, 4.0 g of $CaCO_3.5H_2O$, 2.5 g of peptone. Yeast cells of the desired strains are then added to the culture medium to form a mixture containing $1 \times 10^8$ yeast cells per 1000 ml of culture medium. The yeast cells can be of any of the strains listed in Table 1. In one embodiment, the strain is *Saccharomyces cerevisiae* Hansen IFFI1340. The mixture is then added to the apparatus of FIG. 1.

The activation process of the yeast cells involves the following steps: 1) maintaining the temperature of the activation apparatus at 20–35° C., (e.g., 28–32° C.), culturing the yeast cells for 28 hours; 2) applying an electric field having a frequency of about 10300 MHz and a field strength of 240–260 mV/cm (e.g., about 256 mV/cm) for 16 hours; 3) then applying an electric field having a frequency of about 10312 MHz and a field strength of 330–360 mV/cm (e.g., about 343 mV/cm) for 36 hours; 4) then applying an electric field having a frequency of about 12348 MHz and a field strength of 350–380 mV/cm (e.g., about 367 mV/cm) for 32 hours; 5) then applying an electric field having a frequency of about 12963 MHz and a field strength of 370–400 mV/cm (e.g., about 382 mV/cm) for 36 hours; 6) then applying an electric field having a frequency of about 12987 MHz and a field strength of 330–360 mV/cm (e.g., about 337 mV/cm) for 16 hours; and 7) finally lyophilizing the compositions comprising activated yeast cells to form a powder and storing the powder at 4° C. Preferably, the concentration of the lyophilized yeast cells is more than $10^{10}$ cells/g.

V. Acclimatization of Yeast Cells to the Gastric Environment

Because the yeast compositions of this invention must pass through the stomach before reaching the small intestine, where the effective components are released from these yeast cells, it is preferred that these yeast cells be cultured under acidic conditions to acclimatize the cells to the gastric juice. This acclimatization process results in better viability of the yeasts in the acidic gastric environment.

To achieve this, the yeast powder containing activated yeast cells can be mixed with a highly acidic acclimatizing culture medium at 10 g (containing more than $10^{10}$ activated cells per gram) per 1000 ml. The yeast mixture is then cultured first in the presence of an alternating electric field having a frequency of about 12963 MHz and a field strength of 390–430 mV/cm (e.g., about 416 mV/cm) at about 28 to 32° C. for 28–36 hours (e.g., about 32 hours). The resultant yeast cells are further incubated in the presence of an alternating electric field having a frequency of about 12987 MHz and a field strength of 340–370 mV/cm (e.g., about 356 mV/cm) at about 28 to 32° C. for 16–28 hours (e.g., about 20 hours). The resulting acclimatized yeast cells are then dried and stored either in powder form ($\geq 10^{10}$ cells/g) at room temperature or in vacuum at 0–4° C.

An exemplary acclimatizing culture medium is made by mixing 700 ml of fresh pig gastric juice and 300 ml of wild Chinese hawthorn extract. The pH of the acclimatizing culture medium is adjusted to 2.5 with 0.1 M hydrochloric acid and 0.2 M potassium biphthalate ($C_6H_4(COOK)COOH$). The fresh pig gastric juice is prepared as follows. At about 4 months of age, newborn Holland white pigs are sacrificed, and the entire contents of their stomachs are retrieved and mixed with 2000 ml of water under sterile conditions. The mixture is then allowed to stand for 6 hours at 4° C. under sterile conditions to precipitate food debris. To prepare the wild Chinese hawthorn extract, 500 g of fresh wild Chinese hawthorn is dried under sterile conditions to reduce the water content (≦8%). The dried fruit is then ground (≧20 mesh) and added to 1500 ml of sterile water. The mixture is allowed to stand for 6 hours at 4° C. under sterile conditions. The supernatant is collected to be used in the acclimatizing culture medium.

VI. Manufacture of Yeast Compositions

Figure 2:
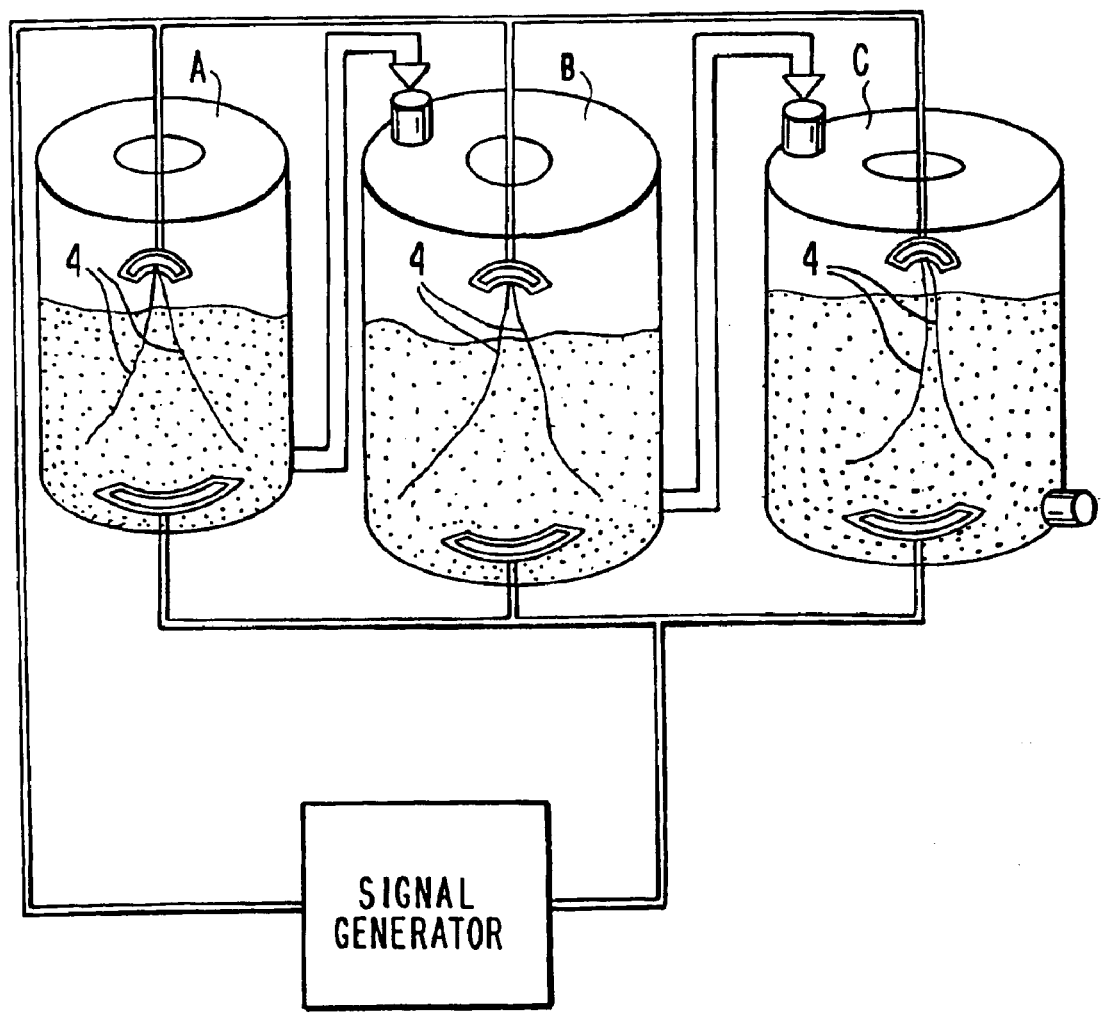
FIG. 2 is a schematic diagram showing an exemplary apparatus for making yeast compositions of the invention. The apparatus comprises a signal generator (such as models 83721B and 83741A manufactured by HP) and interconnected containers A, B and C.

To prepare the yeast compositions of the invention, an apparatus depicted in FIG. 2 or an equivalent thereof can be used. This apparatus includes a first container (A), a second container (B), and a third container (C), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of fruit extracts from *Schisandra chinensis* Baill (wu wei zi), and 100 L of soy bean extracts. To prepare hawthorn, jujube and wu wei zi extracts, the fresh fruits are washed and dried under sterile conditions to reduce the water content to no higher than 8%. One hundred kilograms of the dried fruits are then ground (≧20 mesh) and added to 400 L of sterile water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterile water. The mixture is stirred under sterile conditions at room temperature for twelve hours and centrifuged at 1000 rpm to remove insoluble residues. Once the mixed fruit extract solution is prepared, the solution is sterilized at 121° C. for 30 minutes, and cooled to 40° C. before use.

One thousand grams of the activated yeast powder prepared as described above (Section V, supra) is added to 1000 L of the mixed fruit extract solution, and the yeast solution is transferred to the first container (A) shown in FIG. 2. The yeast cells are then cultured in the presence of an alternating electric field having a frequency of about 12963 MHz and a field strength of about 420–460 mV/cm (e.g., about 435 mV/cm) at 28–32° C. under sterile conditions for 32 hours. The yeast cells are further incubated in an alternating electric field having a frequency of about 12987 MHz and a field strength of 270–290 mV/cm (e.g., about 282 mV/cm). The culturing continues for another 12 hours.

The yeast culture is then transferred from the first container (A) to the second container (B) (if need be, a new batch of yeast culture can be started in the now available first container (A)), and subjected to an alternating electric field having a frequency of about 12963 MHz and a field strength of 400–420 mV/cm (e.g., about 416 mV/cm) for 24 hours. Subsequently the frequency and field strength of the electric field are changed to about 12987 MHz and 320–350 mV/cm (e.g., about 332 mV/cm), respectively. The culturing continues for another 12 hours.

The yeast culture is then transferred from the second container (B) to the third container (C), and subjected to an alternating electric field having a frequency of about 12963 MHz and a field strength of 360–390 mV/cm (e.g., about 372 mV/cm) for 24 hours. Subsequently the frequency and field strength of the electric field are changed to about 12987 MHz and 240–260 mV/cm (e.g., about 256 mV/cm), respectively. The culturing continues for another 12 hours.

The yeast culture from the third container (C) can then be packaged into vacuum sealed bottles of 30–50 ml or 100 ml for use as a dietary supplement, e.g., health drinks, or medication in the form of pills, powder, etc. The dietary supplement can be taken 3–4 times daily at 30–50 ml each time for a period of three months (10–30 minutes before meals and at bedtime). If desired, the final yeast culture can also be dried within 24 hours and stored in powder form.

In one embodiment, the compositions of the invention can also be administered intravenously or peritoneally in the form of a sterile injectable preparation. Such a sterile preparation is prepared as follows. A sterilized health drink composition is first treated under ultrasound (>=18,000 Hz) for 10 minutes and then centrifuged at 4355 rpm for another 10 minutes. The resulting supernatant is adjusted to pH 7.2–7.4 using 1 M NaOH and subsequently filtered through a membrane (0.22 μm for intravenous injection and 0.45 μm for peritoneal injection) under sterile conditions. The resulting sterile preparation is submerged in a 35–38° C. water bath for 30 minutes before use.

The yeast compositions of the present invention are derived from yeasts used in food and pharmaceutical industries. The yeast compositions are thus devoid of side effects associated with many pharmaceutical compounds.

In other embodiments, the compositions of the invention may also be formulated with pharmaceutically acceptable carriers to be orally administered in any orally acceptable dosage form including, but not limited to, capsules, tablets, suspensions or solutions.

EXAMPLES

The following examples are meant to illustrate the methods and materials of the present invention. Suitable modifications and adaptations of the described conditions and parameters which are obvious to those skilled in the art are within the spirit and scope of the present invention.

The activated yeast compositions used in the following experiments were prepared as described above, using *Saccharomyces cerevisiae* Hansen IFF11340 cultured in the presence of an alternating electric field having the electric field frequency and field strength exemplified in the parentheses following the recommended ranges. Control yeast compositions were those prepared in the same manner except that the yeast cells were cultured in the absence of EMFs. Unless otherwise indicated, all yeast compositions and the corresponding controls were administered to the animals by intragastric feeding.

Example 1

Effects on Rats with VaD Induced by Cerebral Ischemia

A large number of clinical studies have shown that blockage in the artery or vein can reduce the blood flow in the brain, thereby inducing cerebral ischemia. When under ischemic conditions for only a few minutes, brain cells can be severely damaged, leading to stroke or dementia and even death. Blockage in the arteria carotis is a major cause in cerebral ischemia. A goal of the treatment is to help the damaged brain cells gradually recover.

In this experiment, VaD is induced by ligation of the common artery on both sides of the neck for 4–12 minutes (the duration depends on the blood flow), which results in memory loss in rats. The change in memory of the rats after administering the activated yeast composition is monitored. The rat VaD model closely resembles human VaD.

Male Wistar rats that were 4–6 months old, weighing 180–200 g were provided by the Chinese Academy of Medical Sciences. Anesthesia of 100 healthy rats was performed by administering abdominally 35 mg/kg (body weight) of chloral hydrate. Then, the necks of the rats were cleaved in the center. Twelve rats were selected for the positive control group (CK1 group), of which the cleaved skin was sealed, and $2\times10^4$ unit/kg (body weight) of penicillin was injected into the buttocks of the rats to prevent infection. For the rest of the rats, the common artery on each side was separated, and clamped to control 50% of the blood flow. After 10 minutes, the clamp was removed and the blood flow in the artery recovered to normal conditions. Then, the cleaved skin of the rats was sealed, and $2\times10^4$ unit/kg (body weight) of penicillin was injected into the buttocks of the rats to prevent infection.

The rats were fed for two days, and the memory of the rats were monitored by using the water maze method. Rats that exceeded 85 seconds in completing the maze were selected. The selected rats were divided into three groups of 12 each, the test group (AY), the control yeast group (NY) and the saline control group (CK2).

Each rat in groups AY, NY, CK2 and CK1 was administered twice daily 1 ml of the activated yeast composition, the control yeast composition and saline (for both CK2 and CK1), respectively for 21 days. The rats were monitored on Day 7, 14 and 21 for the time required to complete the maze. The results are shown in Table 2.

Example 2

Effects on VaD Induced by Blockage of the Middle Cerebral Artery

In this experiment, paraffin oil is injected into the middle cerebral artery of rats. The paraffin oil mimics the microparticles of thrombus and induces blockage of the blood vessel, leading to VaD in the rats. The VaD observed in the rat model is similar to that observed in humans. Through treatment, damaged brain cells recover, and the memory is improved. In this experiment, the Morris maze method was used to record the change in memory after treatment.

Male Sprague-Dawley rats that were 5–7 months old, weighing 220–250 g were provided by the Chinese Medical Science Academy. Anesthesia of 80 healthy rats was performed by administering abdominally 35 mg/kg (body weight) of soluble phenobarbital. Then, the necks of the rats were cleaved in the center. Fifteen rats were selected for the positive control group (CK1). The middle cerebral artery of these rats were slowly injected with 20 µl/kg (body weight) of saline for 10–15 minutes. For the rest of the rats, paraffin oil was slowly injected into the middle cerebral artery for 10–15 minutes at 20 µl/kg (body weight). The paraffin oil was sterilized at 121° C. and cooled to 35 to 38° C. before use. Then, the cleaved skin of the rats was sealed, and $2\times10^4$ unit/kg (body weight) of penicillin was injected into the buttocks of the rats to prevent infection.

The rats were fed for ten days, and the memory of the rats were monitored by the Morris maze method on Day 11. Rats that exceeded 100 seconds in locating the safety zone were selected. The selected rats were divided into three groups of

TABLE 2

| Group | Time for completion of maze before treatment (seconds) (x ± SD) | Time for completion of maze on Day 7 (seconds) (x ± SD) | Time for completion of maze on Day 14 (seconds) (x ± SD) | Time for completion of maze on Day 21 (seconds) (x ± SD) |
| --- | --- | --- | --- | --- |
| AY | 109.3 ± 11.7 | 82.5 ± 9.2 | 61.7 ± 7.4 | 52.4 ± 6.6 |
| NY | 107.4 ± 11.2 | 104.8 ± 10.3 | 103.2 ± 10.8 | 103.7 ± 11.4 |
| CK2 | 108.7 ± 11.5 | 106.6 ± 9.7 | 104.3 ± 9.2 | 105.5 ± 11.2 |
| CK1 | 58.8 ± 7.2 | 51.6 ± 6.8 | 50.6 ± 6.2 | 50.7 ± 6.4 |

The above experiment shows that compared to the groups treated with unactivated yeast composition (NY) or saline (CK2), the group treated with activated yeast composition (AY) demonstrates significant recovery of memory after 7 days, 14 days and 21 days of treatment. On Day 21, the memory of the rats is comparable to those of the rats in the positive control group (CK1).

15 each, the test group (AY), the control yeast group (NY) and the saline control group (CK2).

Each rat in groups AY, NY, CK2 and CK1 was administered twice daily 1 ml of the activated yeast composition, the control yeast composition and saline (for both CK2 and CK1), respectively for 21 days. The rats were monitored on Day 7, 14 and 21 for the time required to locate the safety zone. The results are shown in Table 3.

TABLE 3

| Group | Time for locating the safety zone before treatment (seconds) (x ± SD) | Time for locating the safety zone on Day 7 (seconds) (x ± SD) | Time for locating the safety zone on Day 14 (seconds) (x ± SD) | Time for locating the safety zone on Day 21 (seconds) (x ± SD) |
| --- | --- | --- | --- | --- |
| AY | 146.4 ± 17.8 | 63.6 ± 9.7 | 32.6 ± 6.2 | 18.4 ± 3.6 |
| NY | 144.7 ± 18.2 | 138.2 ± 17.9 | 127.4 ± 16.4 | 129.3 ± 17.3 |
| CK2 | 141.8 ± 16.8 | 133.4 ± 18.2 | 121.3 ± 19.7 | 130.2 ± 16.5 |
| CK1 | 58.8 ± 7.2 | 51.6 ± 6.8 | 50.6 ± 6.2 | 50.7 ± 6.4 |

The above experiment shows that compared to the groups treated with unactivated yeast composition (NY) or saline (CK2), the group treated with activated yeast composition (AY) demonstrates significant recovery of memory after 7 days, 14 days and 21 days of treatment. The group treated with unactivated yeast composition does not demonstrate any effect on the rats compared to the saline control group. On Day 21, the memory of the rats is even better than that of the rats in the positive control group (CK1). Thus, the activated yeast composition helps rats with vascular dementia recover their memory.

While a number of embodiments of this invention have been set forth, it is apparent that the basic constructions may be altered to provide other embodiments which utilize the compositions and methods of this invention.

What is claimed is:

1. A composition comprising a plurality of yeast cells, wherein said plurality of yeast cells are characterized by an increase in their capability to improve the memory of a mammal with vascular dementia as a result of having been cultured in the presence of an alternating electric field having a frequency in the range of about 10280 to 13000 MHz and a field strength in the range of about 200 to 500 mV/cm as compared to yeast cells not having been so cultured.

2. The composition of claim 1, wherein the range of the frequency is about 10280 to 10400, 12320 to 12380 or 12950 to 13000 MHz.

3. The composition of claim 1, wherein the range of the field strength is about 200 to 400 mV/cm.

4. The composition of claim 1, wherein said yeast cells are of the species selected from the group consisting of *Saccharomyces sp, Schizosaccharomyces pombe, Saccharomyces sake, Saccharomyces uvarum, Saccharomyces rouxii, Saccharomyces cerevisiae, Saccharomyces carlsbergensis, Rhodotorula aurantiaca*.

5. The composition of claim 1, wherein said yeast cells are derived from the strain deposited at the China General Microbiological Culture Collection Center with the accession number selected from the group consisting of *Saccharomyces cerevisiae* Hansen AS 2.501, AS2.502, AS2.503, AS2.504, AS2.535, AS2.558, AS2.560, AS2.561, AS2.562 and IFFI1340.

6. The composition of claim 5, wherein said strain is *Saccharomyces cerevisiae* Hansen IFFI1340.

7. The composition of claim 1, wherein the composition is in the form of a tablet, powder or health drink.

8. The composition of claim 1, wherein the composition is in the form of a health drink.

9. A method of preparing a yeast composition, comprising culturing a plurality of yeast cells in the presence of an alternating electric field having a frequency in the range of about 10280 to 13000 MHz and a field strength in the range of about 200 to 500 mV/cm to increase the capability of said plurality of yeast cells to improve the memory of a mammal with vascular dementia as compared to yeast cells not having been so cultured.

10. The method of claim 9, wherein the range of the frequency is about 10280 to 10400, 12320 to 12380 or 12950 to 13000 MHz.

11. The method of claim 9, wherein the range of the field strength is about 200 to 400 mV/cm.

12. A method of improving the memory of a subject with vascular dementia, comprising the step of administering to said subject the composition of any one of claims 1 to 6.

13. The method of claim 12, wherein the administration is through oral administration.

* * * * *

UNITED STATES PATENT AND TRADEMARK OFFICE
CERTIFICATE OF CORRECTION

PATENT NO. : 7,078,202 B2  Page 1 of 1
APPLICATION NO. : 10/717136
DATED : July 18, 2006
INVENTOR(S) : Ling Yuk Cheung It is certified that error appears in the above-identified patent and that said Letters Patent is hereby corrected as shown below:

Column 2, line 38: the expression "IFF11340" should read --IFFI1340--;

Column 2, line 40: the expression "AS 2.501" should read --AS2.501--;

Column 11, line 53: the expression "Vitamin $B_{22}$" should read --Vitamin $B_{12}$--;

Column 14, line 44: the expression "IFF11340" should read --IFFI1340--; and

Column 18, line 7: the expression "AS 2.501" should read --AS2.501--.

Signed and Sealed this

Twenty-first Day of November, 2006

JON W. DUDAS
*Director of the United States Patent and Trademark Office*